United States Patent
Yoo et al.

(10) Patent No.: US 6,519,492 B1
(45) Date of Patent: Feb. 11, 2003

(54) METHOD AND APPARATUS FOR DIRECT IN VIVO GENE TRANSFER BY ELECTROTRANSFECTION

(75) Inventors: James J. Yoo, Brookline; Anthony Atala, Weston, both of MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 09/807,619

(22) PCT Filed: Oct. 15, 1999

(86) PCT No.: PCT/US99/23870

§ 371 (c)(1), (2), (4) Date: Sep. 13, 2001

(87) PCT Pub. No.: WO00/22095

PCT Pub. Date: Apr. 20, 2000

Related U.S. Application Data

(60) Provisional application No. 60/104,403, filed on Oct. 15, 1998.

(51) Int. Cl.[7] .................................................. A61N 1/30
(52) U.S. Cl. ......................................... 604/21; 604/522
(58) Field of Search ............................ 604/501, 20–27, 604/522; 607/116, 152

(56) References Cited

U.S. PATENT DOCUMENTS

| | | | | |
|---|---|---|---|---|
| 5,389,069 A | * | 2/1995 | Weaver |
| 5,501,662 A | * | 3/1996 | Hofmann |
| 5,749,845 A | * | 5/1998 | Hildebrand et al. |
| 5,779,661 A | * | 7/1998 | Stephen et al. |
| 5,807,306 A | * | 9/1998 | Shapland et al. |

* cited by examiner

*Primary Examiner*—Mark Bockelman
(74) *Attorney, Agent, or Firm*—Brobeck, Phleger & Harrison LLP

(57) ABSTRACT

This invention is directed to a novel method for direct in vivo electrotransfection of a plurality of cells of a target tissue. In the method, the target is perfused with a transfection solution. An exterior electrode is positioned so as to surround at least a portion of the target tissue. One or more interior electrodes are placed within the target tissue. The perfusion and the application of the interior and exterior electrodes may be performed in any particular order. After the perfusion and the positioning of the electrodes, both interior and exterior, an electric waveform is applied through the exterior electrode and the interior electrode to transfect the cells in the target tissue.

47 Claims, 14 Drawing Sheets

METHOD AND APPARATUS FOR DIRECT IN VIVO GENE TRANSFER BY ELECTROTRANSFECTION

This application claims the benefit of provisional application 60/104,403 filed on Oct. 15, 1998.

BACKGROUND

1. Field of the Invention

The invention is directed to methods, apparatus and kits for in vivo gene transfer and therapy, in particular by direct in vivo electrotransfection (DIVE).

2. Description of the Background

Transfection is a very important and common technique that is routinely used in modern biomedical and genetic applications. Transfection refers to a method of introducing nucleic acid material into a target cell in a non-lethal manner. Once transfection is used to introduce a nucleic acid into a cell, the nucleic acid may direct synthesis of new RNA and/or new proteins. These RNA and/or proteins may provide new functionality for the cell or suppress the expression of (turn off) other genes.

One of the most important uses for transfection is in gene therapy. Gene therapy refers to the treatment of certain disorders, especially those caused by genetic anomalies or deficiencies, by introducing specific engineered genes into a patient's cells (the host cells). The gene introduced into the cell can treat disorders by expressing a sequence that the host cells, because of its anomalies or deficiencies, cannot express. Thus, for example, the treatment for diabetes may involve transfecting the cells of a diabetic patient with a gene construct that either expresses insulin or induces the expression of insulin. Similarly, sickle cell anemia may be treated by suppressing the expression of the defective sickle cell gene and inducing the expression of normal hemoglobin gene.

Gene suppression may occur by transfecting a gene which encodes a suppressor protein or an antisense nucleic acid construct. A suppressor protein is any protein that reduces or eliminates the expression of another gene. An antisense nucleic acid is a nucleic acid that is complementary to an expressed gene. The complementary nucleic acid may hybridize to the sense RNA of the targeted gene to form non-functional double stranded RNAs which is not translated into protein. In any case, the expression (i.e., translation) of the targeted gene is suppressed by expression (i.e., transcription) of antisense DNA.

Numerous techniques have been developed for transfection of cells in vitro. The basic goal of all transfection techniques is to introduce the nucleic acid into a target cell. Transfection techniques may be broadly classified as either direct or indirect methods. Direct methods involve the manual introduction of nucleic acid. Examples of direct transfection include microinjection or microprojectile transfection. Indirect transfection techniques are numerous but can be broadly classified into viral transfection techniques, liposome transfection techniques and phagocytosis techniques. Successful demonstration of these techniques in vitro has not necessarily been followed by success in vivo.

Direct transfection can be performed by microinjection, microprojectile transfection or by electrotransfection or laser transfection. Microinjection involves the manual injection of nucleic acid solutions into a cell by the use of a small needle (usually a drawn glass capillary) under a microscope. Microprojectile transfection involves the coating small particles with nucleic acid and shooting the particles into a cell with a high velocity gun. Laser transfection or electrotransfection involves puncturing a temporary hole in the cell membrane and allowing nucleic acid in the surrounding media to enter.

Direct transfection is labor intensive. A skilled operator can inject at most, between 200 and 500 cells per day in vitro. Direct transfection by micro injection is difficult or impossible in vivo due to the instability and vibrations of a living subject. Further, the number of cells that can be transfected per day is too small for a significant difference in a living subject. Likewise, microprojectile transfection, a procedure often involving gunpowder and high pressure air, are not practical for use on a patient.

Another disadvantage of current direct transfection techniques is that the procedures are only effective on cells and body parts that can be exposed and accessible to the microinjection needle or microprojectile gun. Thus, the interior of organs such as kidney, brain, bladder, lung and heart cannot be transfected without surgery and concomitant damage to these organs. Laser and electrotransfecting techniques have also not been found to be readily applied to living patients.

The major disadvantage of indirect in vivo transfection is low efficiency. One type of indirect transfection uses viruses to introduce nucleic acid into cells. The viruses most often used include SV40, polyoma, adenovirus, Epstein-Barr, vaccinia, herpes simplex, and retrovirus for mammalian cells and baculovirus, tobacco mosaic virus, cucumber mosaic virus, brome mosaic virus for non-mammalian cells. All viruses currently used in vivo suffer from low transfection efficiency.

An additional disadvantage of viral mediated transfection is the danger of using an infectious agent in a patient. In principle each of these viral techniques may be performed in a way that prevents transmission of infectious virus to the patient. In practice, each technique requires viral recombination in laboratories where inattentive or incompetent personnel may greatly increase the chances for an infectious virus contamination. The use of viruses involves significant risks because some viruses are potent pathogens in their wildtype state and other viruses carry oncogenes in their genomes.

Other potential disadvantages of viral vectors include the limited ability to mediate in vivo (as opposed to it vitro or ex vivo) transfection; the inability of retroviruses to infect non-dividing cells; possible recombination events in replication defective retroviral vectors resulting in infectious retrovirus; possible activation of oncogene or suppression of anti-oncogene due to random insertion, size limitations (less than 15 kb of DNA can be packaged in a retrovirus vector); and the potential immunogenicity of the viral vectors leading to an immune response.

Other indirect transfection methods such as liposome transfection and DNA-calcium phosphate transfection also suffer from low transfection efficiency in vivo. Further, these methods use solutions that may be incompatible with cell survival. In vivo, cell death, which may lead to organ failure, is a significant disadvantage. However, efforts to reduce cell death, such as the rapid introduction and removal of transfection solutions, also reduce transfection efficiency.

Clearly, there is a need for a new in vivo transfection method that can improve the efficiency of target cell transfection without the adverse side effects of current methods. Further, new transfection methods are needed to transfect target cells, such as those in the interior of organs, that are not normally accessible.

SUMMARY OF THE INVENTION

The present invention overcomes many of the limitations, problems and disadvantages associated with current strategies and designs for direct in vivo electrotransfection and provides apparatus, transfection kits, and methods for the direct in vivo electrotransfection (DIVE) transfection of tissues.

One embodiment of the invention is directed to a method for direct in vivo electrotransfection of a plurality of cells of a target tissue with a nucleic acid construct. The target is perfused with a transfection solution comprising a nucleic acid construct. At least a portion of the target tissue is surrounded with an exterior electrode. One or more interior electrode is placed within the target tissue. The perfusion and external and internal electrode may be performed or positioned in any order. An electric waveform is applied through the exterior electrode to transfect the target tissue.

One advantage of the method is the use of a large substantially planar surface as an exterior electrode. The exterior electrode can be wrapped around an organ or wrapped around a body. In contrast to needle or multiple needle electrodes which provide an uneven and localized electric field, the large planar surface electrode can provide a more uniformed electric field which would, in turn, lead to more uniform transfection. Planar means sheet-like. Thus a planar electrode may not be flat, but may be wrapped around an organ like a bandage or a bed sheet.

The transfection solution may be any electrotransfection solution such as physiological saline and/or phosphate buffered saline. The salt content of the transfection solution may be increased or decreased to change the effective propagation of the electric field. This change and adjustment in salt content is particularly useful in a hollow organ, such as a bladder, which is filled with the transfection solution during DIVE.

Another embodiment of the invention is directed to a method for selectively transfecting a subsegment of the cells of a target tissue, which can be an organ, using direct in vivo electrotransfection. In the method, a subsegment of the target tissue is perfused with a transfection solution comprising a nucleic acid construct. An exterior electrode is positioned to surround at least a portion of said target tissue. One or more interior electrodes is placed within the target tissue. Then an electric waveform is applied through the exterior electrode and the interior electrode to cause the transfection of a subsegment of the target tissue. Transfection specificity is maintained because only cells in contact with the transfection solution are transfected. The exterior electrode may be positioned on the skin of the patient if the electric conduction is sufficient. Electric conduction may be facilitated by the application of a electroconductive gel between the exterior electrode and the skin. This method may be useful, for example, if it is only desired to transfect a subsegment of an organ. For example, the bladder lining may be selectively transfected.

Other embodiments and advantages of the invention are set forth, in part, in the description which follows and, in part, will be obvious from this description and may be learned from the practice of the invention.

DESCRIPTION OF THE INVENTION

Figure 1:
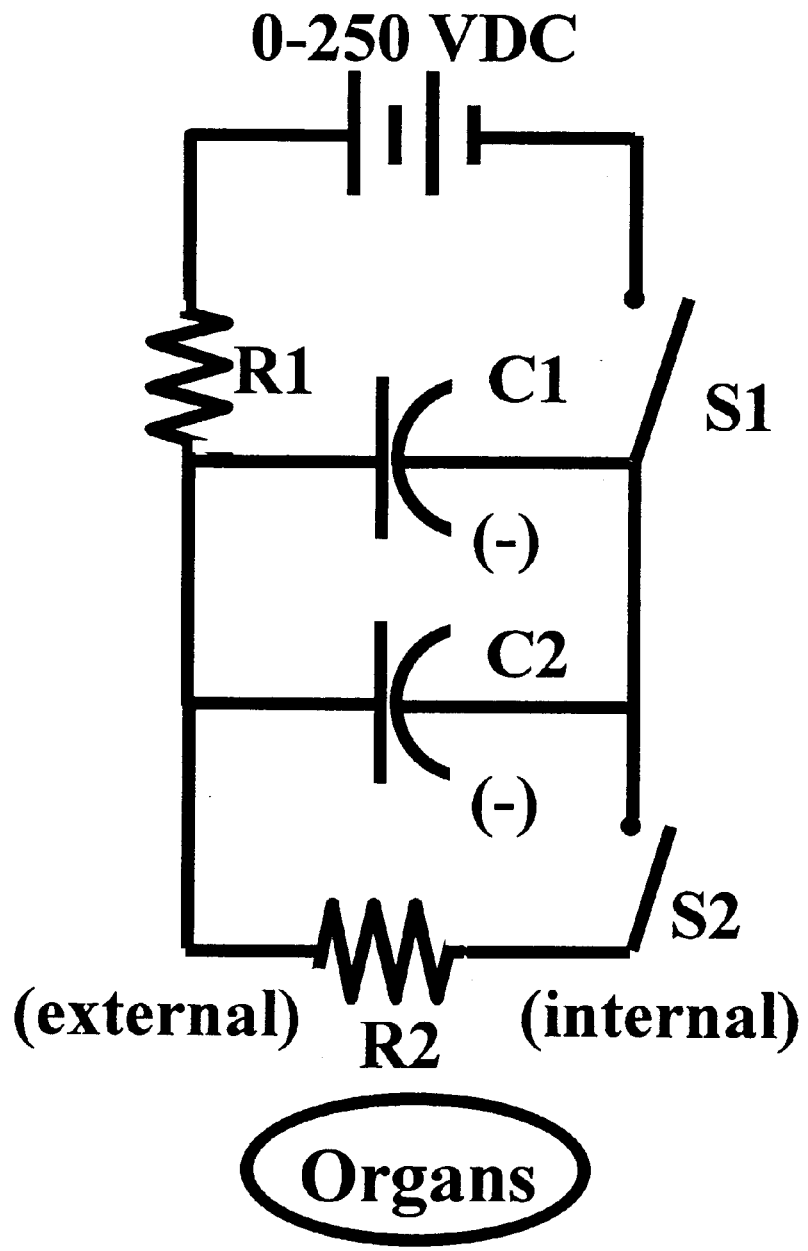
FIG. 1 depicts a schematic diagram of Direct In Vivo Electrotransfection (DIVE) device.
Figure 2:
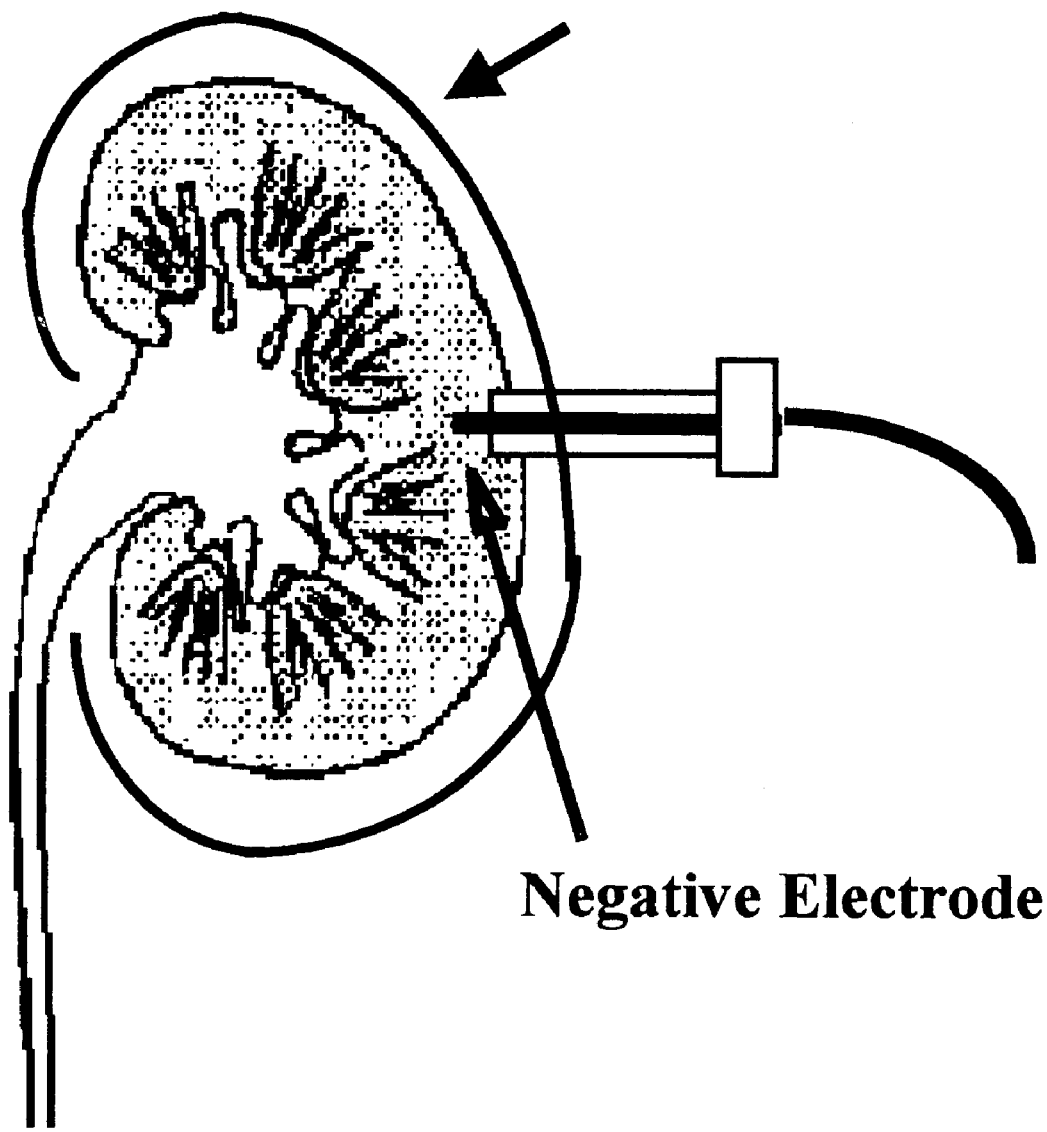
FIG. 2 depict a schematic diagram of an in vivo electrotransfection device in operation. Gene transfer to kidneys is performed via a negative electrode needle through an 18-gauge silastic catheter. A positive electrode is placed externally to the organ.

This invention is directed to a new method of gene therapy that dramatically improves both the transfection efficiency and specificity over current methods.

One embodiment of the invention is directed to a method for direct in vivo electrotransfection of a plurality of cells of a target tissue with a nucleic acid construct. In the method the following three steps (A–C) may be performed in any particular order. (A) The target tissue is perfused with a transfection solution comprising the nucleic acid construct. (B) The target tissue is coated with an exterior electrode. (C) An interior electrode is placed within the target tissue. After the first three steps are accomplished, the target tissue is electrotransfected by applying an electrical waveform to the exterior electrode and the interior electrode. After the electrotransfection, the transfection solution may be optionally removed.

The target tissue may be any tissue in the body that can be surrounded completely or partially by the exterior electrode. Examples of tissues that may be transfected include hematopoietic cells, bone marrow cells, kidney cells, myocytes, hepatocytes, heart, lung, kidney, liver, spleen, thymus, eye, pancreas, stomach, ovary, bowel, testicles, prostate, skeletal muscle skin, lymph nodes, arteries and veins. A target tissue may be the complete organ or a part of an organ. For example, a lobe of the liver may be transfected without transfecting the whole liver, and a portion of a long bone and the bone marrow may be transfected without transfecting the whole bone. Furthermore, where organs exist in pairs, such as the lungs, the kidneys or the testicles, one or both of the organs may be transfected. In addition, more than one organ may be transfected at the same time. For example, the adrenal glans are positioned near the top of the kidneys. Thus, the adrenal gland and the whole or part of the kidney may be transfected in the same procedure.

The perfusion solution may be any solution which is suitable for electrotransfection in the method of the invention. In particular, the perfusion solution will not irreversibly inactivate the nucleic acid within the time frame of the electrotransfection process, nor will the perfusion solution be unduly toxic to the patient. Examples of suitable electrotransfection solution include phosphate buffered saline and physiological saline.

Perfusion may be performed using a hollow needle or cannula. In one embodiment, the perfusion needle may be connected to a reservoir of transfection solution by a pump. A needle and syringe may also be used. Any perfusion technique known to those of skill in the art may be used. For example, in the perfusion of the bladder, the bladder may first be voided, and the interior volume of the bladder may be filled with electrotransfection solution by a needle or catheter. Similarly, in a kidney, the blood supply may be temporarily blocked while a perfusion solution is injected into the kidney. Similarly, a transfection solution may be injected into the effluent vessels of the kidney to perfuse the kidney. Further, a perfusion solution may be injected into a sub-region of an organ, if it is desired to transfect only a portion of the target tissue. Different tissues may be sensitive to the duration of the procedure. The heart and the kidney may not be able to withstand prolonged blockage of a blood supply. In contrast, a skeletal muscle of a limb may remain viable even if the blood supply is removed for over an hour.

One advantage of the invention is that the method may be used for the electrotransfection of solid organs such as liver, semi-solid organs such as kidney and lung, and hollow organs such as bladders.

The exterior electrode may be made from any conductor which is not toxic to the patient. Examples of materials that may be used for the exterior electrode include metal foil made from aluminum, gold, platinum, silver, and/or copper. While some metals such as copper are toxic if left in the body for long periods, they may nevertheless be used if the electrotransfection procedure is performed in a short time.

In another embodiment of the invention, the exterior electrode may be a plurality of wires or a wire mesh. It is known that a wire mesh of sufficiently small grid size will behave electrically in a similar fashion to a conducting sheet. Thus, in situations where the organ is hard to reach or the electrode material is expensive, the exterior electrode may comprise one or more electrically connected wires.

Another embodiment of the invention is directed to a direct in vivo electrotransfection technique where, the exterior electrode only covers a portion of the target organ. For example, as shown in FIG. 9, the transfection of a kidney may be performed with the exterior electrode covering one-half, one-fourth, or one eighth of the exterior surface of the kidney. With this method, only a portion of the cells in the target organ is transfected. Alternatively, the exterior electrode may cover only one side of the organ, for instance by placing a kidney-shaped exterior electrode on the skin adjacent to the kidney.

The interior electrode may be any electrode that can electrically connect with the interior of the target tissue encapsulated by the exterior electrode. In a preferred embodiment, the interior electrode may be a needle.

In an embodiment of the invention, the interior electrode may have a sharp end to facilitate placement of the interior electrode. An electrode with a sharp end may be positioned directly into the interior of a target tissue by puncturing the skin and the surface of the tissue.

In another embodiment of the invention, the interior electrode may be a flexible catheter. One advantage of a catheter is that it may be introduced into the body at a location distal to the final position. For example, in the transfection of the bladder, the catheter may be introduced through the urethra to reach the interior of the bladder. Similarly, the transfection of the intestine or the stomach may be performed using a catheter as the interior electrode.

In another embodiment of the invention, the interior electrode may be hollow to allow the passage of a perfusion solution. A perfusion solution such as the transfection solution may be injected through the hollow interior electrode into the target tissue. In effect, the interior electrode may also serve as a perfusion needle.

To prevent direct electrical contact between the exterior electrode and the interior electrode, one or both electrodes may be insulated where they may come into contact during electrotransfection. Insulation can comprise any material that forms a coating which does not conduct electricity. Insulation techniques may include wrapping the electrode with a non-conductive material such as TEFLON®, PCV and silicon and the like. To allow electrotransfection, the insulated interior electrode must have an uninsulated tip. The uninsulated tip may resemble a point, formed, for example, by coating the length of a linear electrode (i.e., in the shape of a very thin pencil) with insulation except for the last millimeter or less of the electrode. Alternatively, if it is desired, the last centimeter or longer of the interior electrode may be left uninsulated to provide for larger area for electrotransfection. An elongated uninsulated region may be desirable in the transfection of an elongated organ, such as the kidney.

A plurality of electrical waveforms may be used for transfecting the target tissue. For example, the waveform may comprise alternating current or direct current. Both alternating current and direct current may also have a voltage or current profile over time that resemble a sine wave, a sawtooth wave, a square wave, a ramp wave, a reverse ramp wave or a more complex wave form. Either or both polarity arrangements of the electrodes may be used. That is, the exterior electrode may be positive relative to the interior electrode or the exterior electrode may be negative relative to the interior electrode. The electrotransfection waveform may consist of a single pulse or more preferably a series of pulses having these profiles.

The electrical waveform generator may be custom designed or commercially available electrical waveform generator. In one embodiment, the electrical waveform generator is one or more capacitors connected in series or in parallel. The capacitors are charged using a charging circuit. After the electrodes are in place, electrotransfection may be performed by attaching the electrodes to the waveform generators—which are made up of charged capacitors. To control the current flow, a resistor may be connected in series with the electrode during electrotransfection.

It is known to those of skill that the electrical circuit of FIG. 1 may be replaced with an equivalent electrical circuit. For example, the two parallel capacitors may be replaced by one large capacitor or a plurality of capacitors connected in series or in parallel to achieve the same results. The power supply may be a battery, or a capacitor charged to the correct voltage, or an AC powered DC power supply. The resistors may be replaced by a plurality of resistors connected in series and in parallel to achieve the same resistance. Switches one and two may be simple knife edge switches, electromechanical relays, semiconductors switches such as transistors or triacs. The switches may further incorporate anti-arcing circuits and debouncing circuits and the like to control the flow of electricity at the moment of switch closure or opening. Furthermore, the complete circuit may be replaced by a computer controlled power supply with voltages controlled by a digital to analog converter. In that way any desirable waveform may be generated and stored in the computer and repeated one or multiple times to achieve the same results. It is also known that if the analog to digital converter or the computer controlled power supply cannot generate sufficient current, emitter follower circuits can be used to supply the deficient current. It is also known that a computer controlled power supply may be set up to regulate voltage, current, power, or a mixture of these parameters in both direct and alternating current formats. Any or all combination of such electric devices are contemplated and known to those of skill in the art.

In an embodiment of the invention an electrically conductive gel is placed between the exterior electrode and the target tissue to facilitate electrical contact. The electrically conductive gel may be any one of a number of commercially available non-toxic gel solutions which are conductive to electricity.

Electrotransfection may be performed once or a plurality of times. One pulse of electrotransfection may be desirable for the prevention of tissue destruction. If it is desired to increase the transfection efficiency, or if cell death is not a primary concern, electrotransfection may be performed up to, for example, ten times, one hundred times, one thousand times, ten thousand times or more. If electrotransfection is performed more than once, the electrotransfection may be performed over a number of weeks. In such cases, the interior electrode, the exterior electrode, the perfusion needles or any combination of these items may optionally be left attached to the target tissue.

Another embodiment of the invention is directed to an apparatus for the in vivo electrotransfection of a target tissue. The apparatus comprises an exterior electrode, an interior electrode, and a perfusion needle or cannula. In a particular embodiment, the interior electrode serves as a perfusion cannula.

In a preferred embodiment of the invention, the in vivo electrotransfection apparatus is a one piece device designed to facilitate the endoscopic transfection of a target tissue. One form of this device is shown in FIG. 8. One advantage of such an-apparatus is that only a small incision is needed for electrotransfection. Further, if the exterior electrode is applied to the skin and the perfusion needles and interior electrode have sharp ends, no incision is necessary because the interior electrode and the perfusion needles can gain entry by puncturing the skin with the sharp end. Thus, this apparatus enjoys all the benefits of endoscopic surgery, such as more rapid healing, shorter hospital stay and minimal discomfort for the patient. One embodiment of such an apparatus can further comprise an outer sheath housing a plurality of electrically connected wires that are retractable. When extended, the wires form a spoke-like pattern radiating from the center of the sheath. Within the sheath there is a centrally located interior electrode. In operation, the functional end of the apparatus is inserted into a position adjacent to a target tissue. The interior electrode is extended to puncture the interior of the target tissue. The target tissue may be perfused by a transfection solution delivered through the hollow interior electrode. Alternatively, additional perfusion may be performed by additional perfusion needles. The radial wires are extended to surround the targeted tissue, a plurality of electrically connected wires of sufficient density have an electrical behavior similar to that of a continuous conductor. Optionally, a electroconductive gel may be injected to facilitate electrical contact between the radial wires and the outside of the target tissue. The electroconductive gel may be delivered via the sheath that houses the radial wires. Electrotransfection is then performed by applying an electrical waveform to the interior electrode and to the radial wires which function as the exterior electrode.

Another embodiment of the invention is directed to a kit for direct in vivo electrotransfection. The kit may comprise an exterior electrode, an interior electrode, and a transfection solution. A DNA construct to be transfected may be included in the kit or may be supplied by the user. In operation, a DNA construct is diluted into the transfecting solution and the transfecting solution is used to perfuse a target tissue. The exterior electrode is applied to encapsulate the target tissue. The interior electrode is positioned in the interior of the target tissue. One or more electrical waveforms are applied to the electrodes to electrotransfect the target tissue. In an embodiment of the invention, the kit may be tailored for specific gene therapy usage. For example, a kit containing a pancreas shaped exterior electrode and a DNA construct for the expression of insulin may be used for the treatment of diabetes. Alternatively, a kit may be a general purpose kit comprising a pliant metal foil that the user can shape to fit a particular organ. The user may supply the nucleic acid construct, or the kit may include a plurality of constructs for different forms of gene therapy The DNA construct used for the methods, kits, and apparatus of the invention may comprise a construct that expresses a gene. A gene is a nucleic acid sequence which encodes a sequence from which an RNA molecule may be transcribed by a nucleic acid polymerase. While most genes have an associated promoter region, there are some genes in which either do not have promoters or do not have an identifiable promoter.

The DNA construct may also contain regulatory nucleic acid sequences such as a promoter, ribosome binding sites, capping signals, transcription enhancers and polyadenylation signals, initiation, termination and, and operator sequences, ribosome binding sites, capping signals, transcription enhancers and polyademylation signals. Regulatory sequences 5' of the transcription initiation codom are collectively referred to as the promoter region. The sequences which are transcribed into RNA are the coding sequences. The RNA may or may not code for a protein RNA that codes for a protein is processed into messenger RNA (mRNA). Other RNA molecules may serve functions or uses without ever being translated into protein. These include ribosomal RNA (rRNA), transfer RNA (tRNA), and the antisense sense RNAs. In eukaryotes, coding sequences between the translation start codon (ATG) and the translation stop codon (TAA, TGA, or TAG) may be of two types: exons and introns. The exons are included in processed mRNA transcripts and are generally translated into a peptide or protein. Introns are excised from the RNA as it is processed into mature mRNA and are not translated into peptide or protein.

The DNA construct may contain a gene that contains introns and exons as may be obtained from genomic DNA. Alternatively the gene may have the introns excised from the DNA, as may be obtained from cDNA. Further, the gene within the DNA construct may contain anti-sense DNA—DNA that encodes antisense RNA. Anti-sense RNA is RNA that is complementary to or capable of selectively hybridizing to some specified RNA transcript. Thus, anti-sense RNA for a particular gene would be capable of hybridizing with that gene's RNA transcript in a selective manner. Finally the DNA construct may contain an anti-sense gene—a segment of anti-sense DNA operably joined to regulatory sequences such that the sequences encoding the anti-sense RNA may be expressed.

The DNA construct may contain a gene and a promoter region which is joined so as to place the expression or transcription of the coding sequence under the influence or control of the promoter region. Further a promoter region can be joined to a coding sequence such that the promoter region is capable of effecting transcription of that coding region such that the resulting transcript might be translated into the desired protein or polypeptide.

The precise nature of the regulatory sequences needed for gene expression in different target tissue may vary between species or cell types, but shall in general include, as necessary, 5' non-transcribing and 5' non-translating sequences involved with initiation of transcription and translation respectively, such as a TATA box capping sequence, CAAT sequence, and the like. Especially, such 5' non-transcribing regulatory sequences will include a promoter region which includes a promoter sequence for transcriptional control of the operably joined gene. Such transcriptional control sequences may also include enhancer sequences or upstream activator sequences, as desired.

The DNA construct may be made from a vector using recombinant DNA techniques. A vector may be any of a number of nucleic acid sequences (some of which are available commercially) into which a desired sequence may be inserted by restriction and ligation. Vectors are typically composed of DNA although RNA vectors are also available. Vectors include plasmids, phage, plasmids and cosmids.

A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to a promoter region and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., beta-galactosidase or alkaline phosphatase), and genes which visibly affect the phenotype of transformed or transfected cells, hosts, colonies or plaques. The DNA construct may be made using any of a great number of vectors known to those of ordinary skill in the art.

It is within the knowledge and ability of one ordinarily skilled in the art to recognize, produce and use fragments of nucleic acid sequences. including vectors and genes and promoter sequences and the like to produce a DNA construct purposes such as gene expression, antisense RNA production, and the like. Techniques for such manipulations are well known in the art and may be found, for example, in Sambrook, et al., Molecular Cloning, A Laboratory Manual, 2d ed., Cold Spring Harbor Laboratory Press, Plainview, N.Y. (1989). A great variety of cloning vectors, restriction endonucleases and ligases are commercially available and their use in creating DNA libraries is well known to those of ordinary skill in the art. See, for example, Sambrook, et al., Molecular Cloning, A Laboratory Manual, 2d ed., Cold Spring Harbor Laboratory Press, Plainview, N.Y. (1989).

The DNA construct may contain constitutive promoters or regulated promoters. Constitutive promoters express a sequence continuously while regulated promoters only express under specific conditions. For example, in a DNA construct comprising regulated promoters, transcriptional initiation regulatory sequences can be selected which allow for repression or activation, so that expression of the downstream sequences can be modulated. Such regulatory sequences include regulatory sequences which are temperature-sensitive or chemical sensitive so that by varying the temperature or by injecting a chemical gene expression can be repressed or initiated. Also the DNA construct may comprise two genes that are transcribed in opposite directions such that the expression of one gene results in antisense expression of the second gene. In such a construct, the induction of one gene is accompanied by repression or the expression of the second gene. Further, it is known that regulatory sequences may comprise DNA elements which confer tissue or cell-type specific expression.

Selection and manipulation of particular DNA sequences for use in this invention is a routine matter, in view of the particular disease to be treated.

Demonstration of gene expression by the luciferase activity assay in the percutaneous electrotransfected kidneys of Example 1 below shows that the gene transfer may be accomplished by a minimally invasive technique. There is basically no renal disease which would not be of potential interest for a therapeutic use of gene transfer ranging from acute inflammatory diseases to chronic renal diseases. Kidney is also an attractive target organ for gene delivery. One of the two kidneys can be genetically-modified selectively. Using minimally invasive technique, gene transfer can be repeated a number of times with less concern for potential immunogenicity. In addition, the selective gene transfer to specific cell type may be achieved.

Gene transfer to bladders using DIVE results in a successful delivery of genes to a full layer of urothelial cells. Interestingly, no evidence of gene expression was noted in the submucosal and smooth muscle layer. There was no evidence of gene expression in the PBS-treated control bladders and other retrieved distant organs. The Examples show a successful gene transfer with the peak expression at day 7 after the transfection. β-galactosidase staining of adenoviral mediated gene transferred bladder using X-gal demonstrated sporadic positively stained blue cells in superficial layers of the smooth muscle and epithelium.

The method of the invention which allows intraluminal gene transfer to a bladder offers many advantages. It allows organ confined local delivery of genes without any systemic side effects. Because electroporation does not involve viruses and other foreign proteins, gene delivery to bladders can be repeated as many times as needed and does not need to be concerned with possible antigenicity. The successful gene transfer to kidneys using minimally invasive technique suggests that this system may also be performed in bladders per urethra. Numerous bladder diseases may benefit from the direct gene transfer by electrotransfection. These include inflammatory conditions such as cystitis and fibrosis. Applying this system in bladder tumors would be an attractive option. Superficial bladder tumors originate from the epithelial cells and this system may be an ideal choice because the gene delivery can be limited to the urothelial layers only and does not affect any deeper layers of the bladder.

Other embodiments and advantages of the invention are set forth, in part, in the description which follows and, in part, will be obvious from this description and may be learned from practice of the invention.

EXAMPLES

Example 1
Nucleic Acid Constructs

In the following examples, two different vector systems, pGL3 and pCMV were used. pGL3 (Promega Co., Madison, Wis.) contains a reporter gene encoding firefly luciferase, expressed by a SV40 promoter-enhancer. pCMV13 (Clonetech Laboratories, Inc., Palo Alto, Calif.) contains a *Escherichia coli* β-galactosidase, driven by CMV promoter-enhancer. Plasmids were prepared by standard alkaline lysis technique followed by ethanol precipitation. Phosphate buffered saline (PBS) was used as the electrotransfection buffer. 100 μg DNA was used in each electrotransfection.

Example 2
Animal Model and Gene Transfer Technique

Male Sprague Dawley rats, weighing approximately 250 grams, were used in this study. Gene transfer to rat kidneys and bladders was accomplished via direct local injection with an 18-gauge silastic angiocatheter. After the introduction of 100 μg DNA into each kidney and bladder, organ contact was achieved via a negative electrode needle inserted through the sheath. A positive electrode was placed externally. Electrotransfection was performed with a electric waveform generator specifically designed for.this study, using a one millisecond pulse (100 volts, 25 watts, 25 mAmp).

The electric waveform generator was equipped with capacitors that can be charged in parallel through a limiting resistance to the desired voltage. The capacitors were subsequently disconnected from the power supply and discharged through an electrode needle to the organ being studied (FIG. 1). Based on the fact that electric current flows between electrodes, this system was designed to transmit mild electrical pulses to the entire target organ by discharging electric current through an interior electrode needle towards the exterior electrode which encases the entire organ externally. The electrical pulse was discharged to the target organ through a single small gauge needle. This enabled the current to travel omnidirectionally from the centrally located interior electrode towards the surface of the target organ. Electrical pulses were generated by discharging a capacitor through tissue composed of cells and parallel load resistor. For the purpose of this set of experiments, the electric waveform generator was equipped with two 560 microfarad (μF)/250 volt electrolytic capacitors that were charged in parallel through a limiting resistance to the desired voltage, 100 volts direct current (VDC). They were then disconnected from the power supply and discharged through the organ being studied (FIG. 1). A single electrotransfection session was performed per animal.

To determine the optimal current of delivery, we performed an in vivo electrotransfection in kidneys and bladders with pGL3. Electric currents of 0, 50, 100 and 200 volts were given at 1 millisecond pulse, 25 watts, 25 mAmp. A fixed dosage of 100 μg pGL3 was given in each animal and consequently, the animals were retrieved at post transfection days 3 and 7 for kidneys and bladders, respectively. Organs were snap-frozen in liquid nitrogen for subsequent luciferase activity assay.

Figure 7:
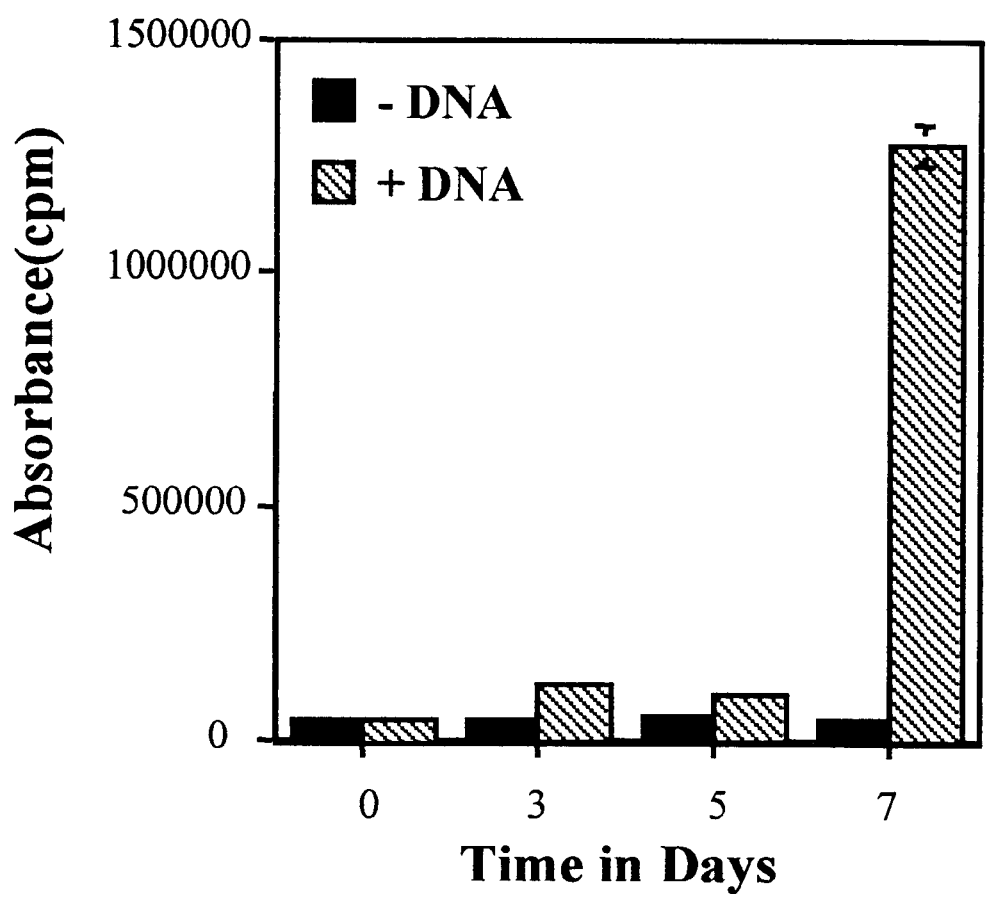
FIG. 7 depicts the time course of luciferase gene expression in bladder tissue after direct in vivo electrotransfection.
Figure 8A:
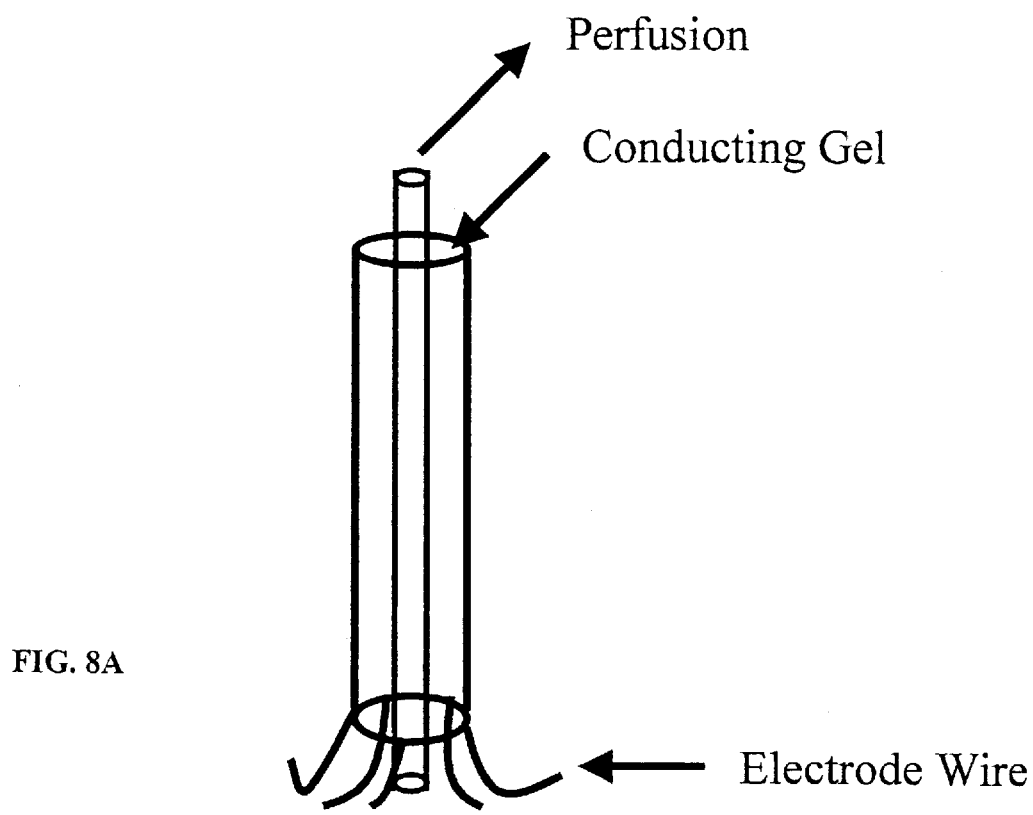
FIG. 8 depicts an apparatus for use in performing electrotransfection according to one embodiment of this method.
Figure 8B:
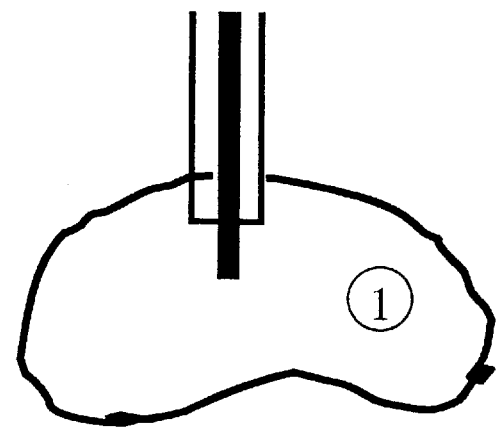
Figure 8C:
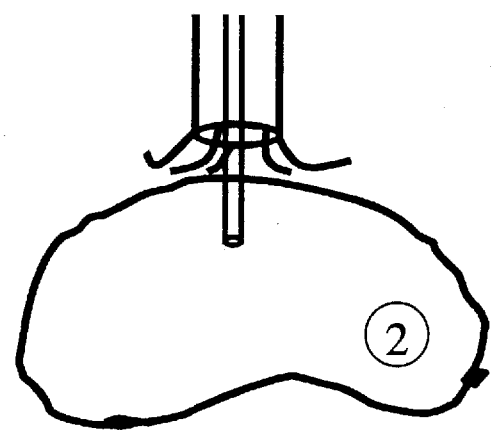
Figure 8D:
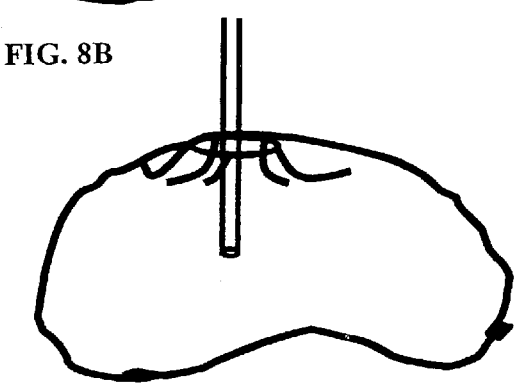
Figure 9A:
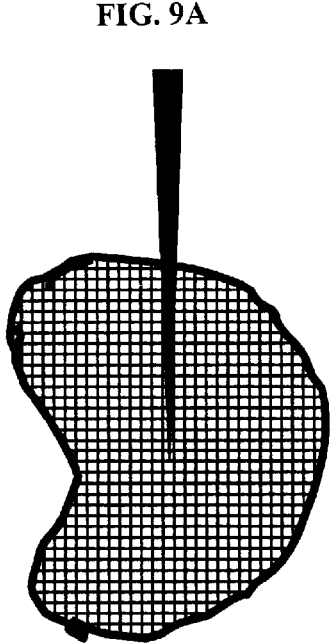
FIG. 9 depicts the use of an exterior electrode and an elongated interior electrode which surround various portions of the target organ.
Figure 9B:
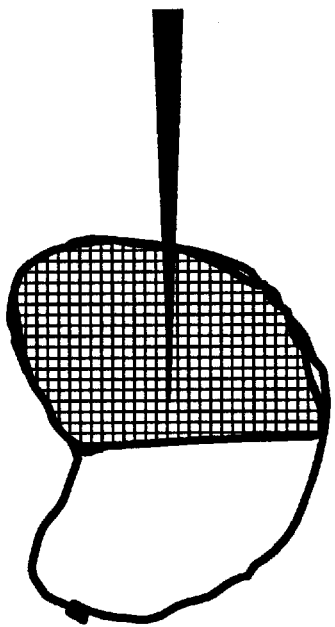
Figure 9C:
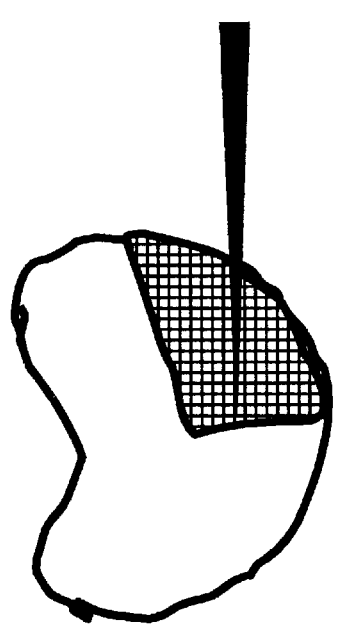
Figure 9D:
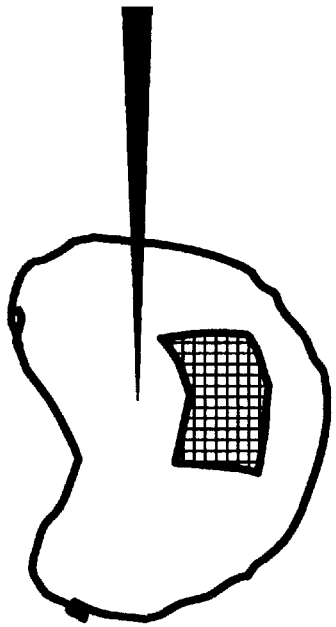
Figure 9E:
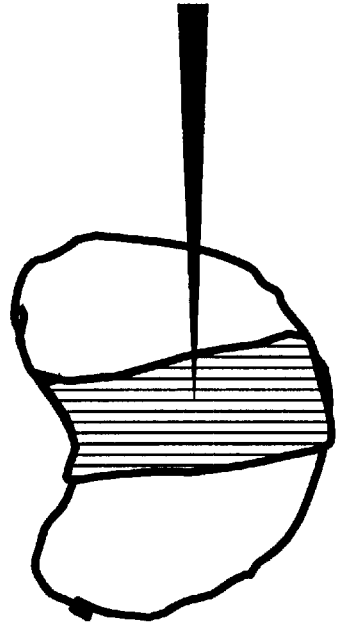

Retrieved rat kidneys and bladders, electrotransfected with pGL3, were minced in a tissue grinder and lysed in 1×lysis buffer (25 mM Tris, pH 7.8 with H3PO4, 2 mM CDTA, 2 mM DTT, 10% glycerol, and 1% Triton X-100) at room temperature for 15 minute. Following centrifugation, 20 μl of protein lysates were mixed with 100 μl of substrate (Promega Co., Madison, Wis.) consisting of 270 μM Coenzyme A (lithium salt), 470 μM Luciferin, and 530 μM ATP. Luciferase activity was measured by scintillation counter as a function of counts per minute (cpm). The results of these tests are shown in FIG. 7.

To determine the time course of reporter gene expression, gene transfer to kidneys and bladders was performed using pGL3. A parallel set of kidneys and bladders were electrotransfected with PBS alone as controls. Rat kidneys, bladders and other organs (liver, spleen and testis) were retrieved at 0, 3, 5 7, 10 and 14 days after the procedure for luciferase activity assay.

To determine the feasibility of performing direct in vivo gene transfer using a less invasive approach, a conducting pad placed on the back of the animal was used as a positive electrode. 100 μg of pGL3 promoter-reporter gene construct was infused percutaneously into the renal parenchyma. The negative electrode rod was then inserted through the silastic sheath and electrotransfection was performed immediately using the same parameters stated in the above experiment. PBS was injected as a control in separate set of kidneys. Rat kidneys were retrieved at 3 days after the procedure for luciferase activity assay.

Example 3
Immunocytochemistry

To determine cellular patterns of gene expression in electrotransfected organs, kidneys and bladders were electrotransfected with pCMVβ DNA vector expressing the *Escherichia coli* β-galactosidase gene. Retrieved kidneys and bladders were thoroughly flushed in phosphate buffer saline (PBS) and frozen in OCT embedding compound (Miles Incorporated Diagnostic Division, Elkhart, Ind.). Six-micrometer cryostat sections were fixed in 4% paraformaldehyde for 10 minutes and subsequently stained with X-gal (5-bromo-chloro-indolyl-β-galactosidase). β-galactosidase cleaves this substrate into an indigo compound, such that cells producing the transferred β-galactosidase gene product are stained blue. Working solution for X-gal consisted of 10 mM $K_3Fe(CN)_6$, 10 mM $K_4Fe(CN)_6$, 2 mM $MgCl_2$, 0.02% NP-40, 0.01% Na-deoxycholate and 0.4 mg/ml x-gal in dimethylformamide. Immunocytochemistry was performed with a mouse monoclonal anti-β-galactosidase biotin conjugate (Sigma, St. Louis, Mo.) using USA ultra streptavidin detection system (Signet Laboratories, Inc., Dedham, Mass.). Cryostat sections of 6-micrometer were stained with an antibody dilution of 1:500 in PBS with 0.1% bovine serum albumin. Subsequently, the tissue sections were counterstained with hematoxylin.

Example 5
Reverse-transcription PCR for RNA Analysis

To demonstrate the functional efficacy of the electrotransfection, RT-PCR was performed from the retrieved kidneys and bladders. RNA was extracted using a standard TRIzol method with some modifications (Chomezynski, R. and Sacchi, N. *Analytical Biochemistry* 162: 156, 1987). Kidneys and bladders were homogenized in TRIzol reagent and RNA was precipitated with isopropyl alcohol as previously described. Subsequently, RNA was mixed in a solution consisting of 1×PCR buffer (Boehringer Mannheim Co., Indianapolis, Ind.), 0.01 U/µl RNase inhibitor, and 0.04 U/µl DNase 1 (GIBCOBRL, Grand Island, N.Y.). Reaction mixture was incubated at 37° C. for 30 minute. Immediately after the incubation, 0.25 µg/µl of proteinase K (Ambion Inc., Austin, Tex.) was added to the reaction mixture and incubated again for 30 minute. After the precipitation of RNA, cDNA synthesis was performed using oligo d(T) primer as described by manufacture (Clontech, Palo Alto, Calif.). PCR reaction was conducted using amplification cycle profile consisting of 94° C. for 1 minute, 62° C. for 1 minute, and 72° C. for 2 minute for each cycle. Following 30 cycles of PCR thermal protocol, additional cycle at 72° C. for 7 minute. was performed to ensure complete DNA extension.

Figure 6:
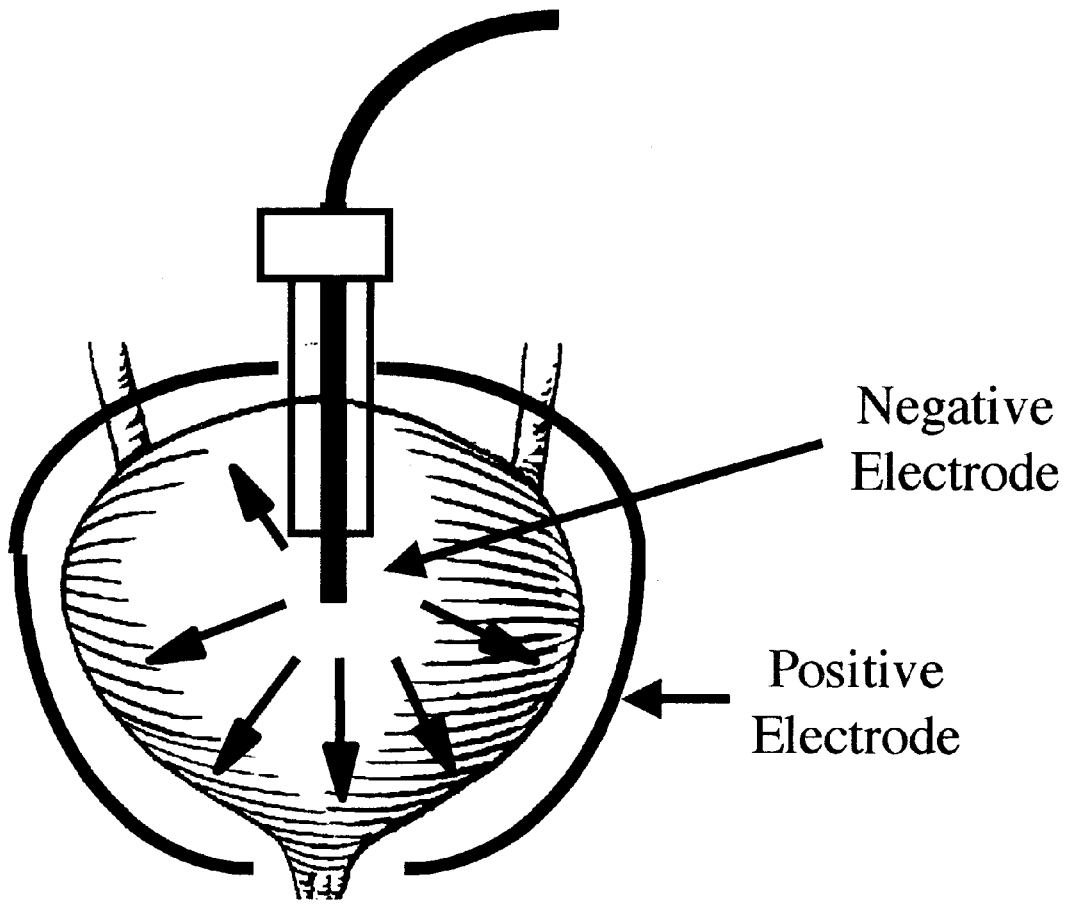
FIG. 6 depicts the direct in vivo electrotransfection of a bladder.

Reverse transcription-PCR products corresponding to the predicted sized of 500 base pairs were obtained from RNA isolated from electrotransfected bladders (FIG. 6, lane 2) and kidneys (FIG. 6, lane 4). The control bladders (FIG. 6, lane 3) and kidneys (FIG. 6, lane 5) failed to show any β-galactosidase mRNA. The positive control, β-galactosidase plasmid, was run in lane 1.

Example 6
In Vivo Electrotransfection of Testes

To determine whether an in vivo electrotransfection could be performed in a less invasive method into kidneys, the kidneys were transfected percutaneously through an 18 gauge angiocatheter. The optimal electrical current to achieve most effective gene transfer was determined by treating with various current settings ranging from 0 to 200 volts direct current with fixed dose of 100 µg pGL3.

Figure 4:
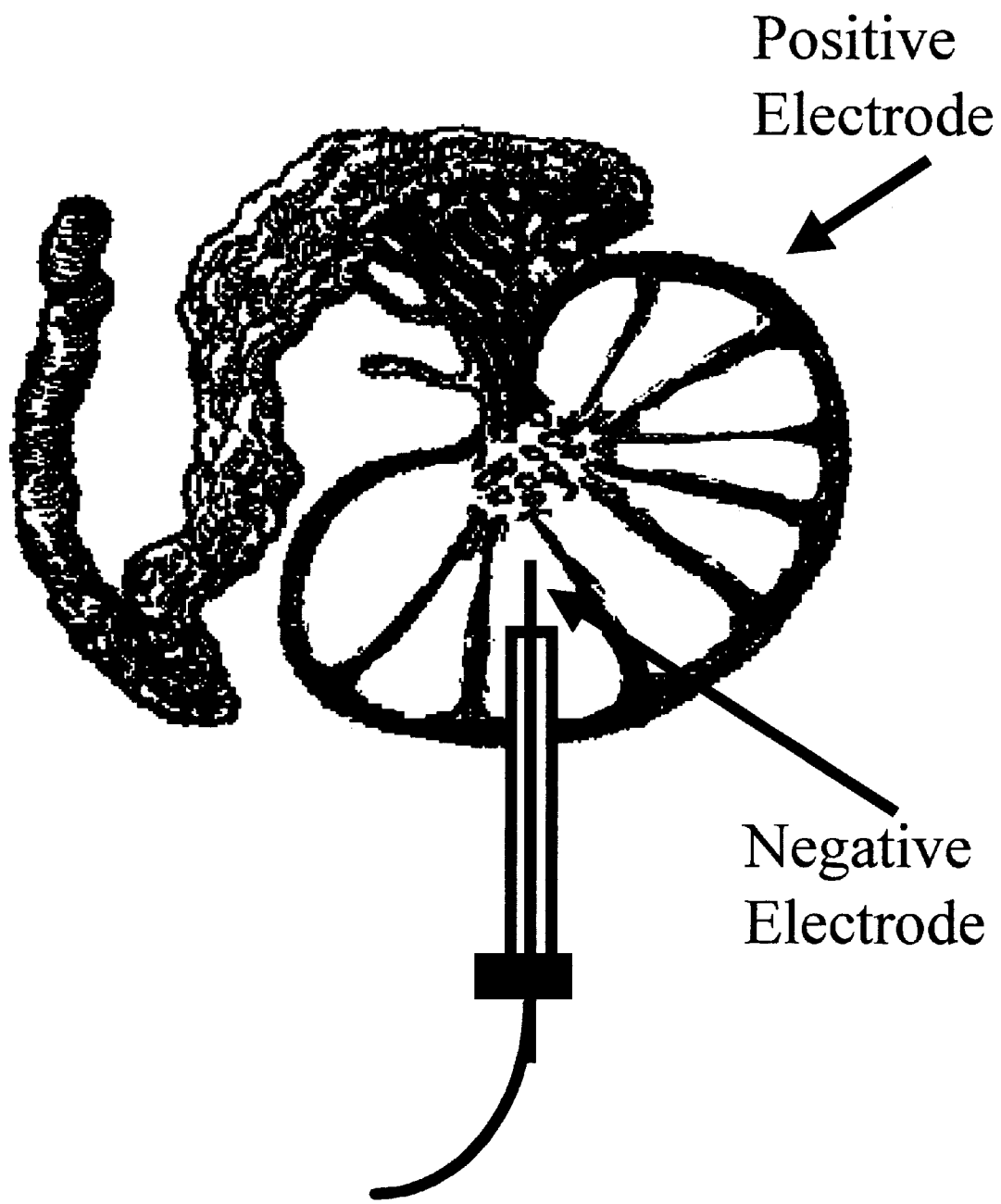
FIG. 4 depicts the direct in vivo electrotransfection of a testicle.

Gene transfer to rat testes was accomplished via direct local injection with an 18 G silastic angiocatheter. PGL3 luciferase and (3-galactosidase reporter gene constructs were used. After the introduction of 100 µg DNA into each testis, organ contact was achieved via a negative electrode needle. A positive electrode was placed externally (FIG. 4). Electrotransfection was performed using a one millisecond pulse (100 volts, 25 watts, 25 mAmps). Gene transfer to the testes was performed unilaterally. Direct injection of DNA was performed on the contralateral testis as a control. The rat testes and other organs (liver, spleen and bladder) were retrieved at 0, 1, 3, 5, 7.10 and 14 days after the procedure. All animals survived without any complications. Successful gene transfer was confirmed by luciferase activity assay, histochemical staining for β-galactosidase, and by reverse transcription polymerase chain reaction (RT-PCR) with primers specific for galactosidase mRNA.

Figure 5:
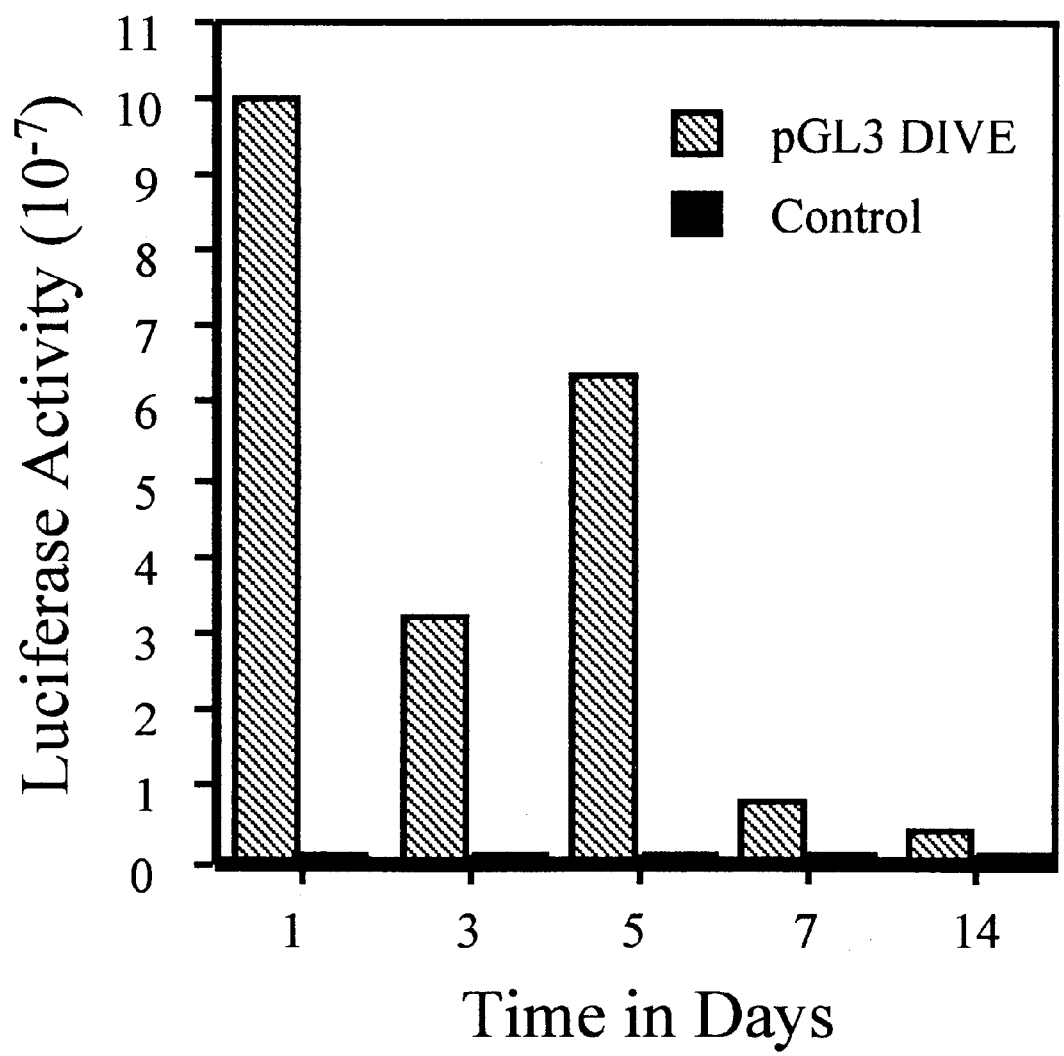
FIG. 5 depicts the time course of luciferase gene expression in rat testes after direct in vivo electrotransfection at days 1, 3 and 5.

At retrieval, the transfected organs appeared normal grossly and histologically. To investigate the time course of expression, luciferase activity was measured at various time points after the electrotransfection. Significant luciferase activity was expressed at 1, 3 and 5 days after electrotransfection, and continued throughout the course of the study (FIG. 5). The control animals showed only minimal expression at days 1 and 3, and returned to basal levels by day 5. Distant organs did not show any luciferase activity. Positive β-galactosidase enzyme activity was observed in the transfected testicular cells. RT-PCR products from the transfected testes were observed indicating the successful transcription of mRNA This study demonstrated that effective gene delivery to intact testes is feasible using a system of direct organ confined gene transfer by electrotransfection. The system using DIVE device is a simple, safe and effective method for delivering genes to appropriate target tissues and may increase the potential clinical utility of gene-based therapies for testicular disorders.

Example 7
Transfection Efficiency Analysis

Figure 3:
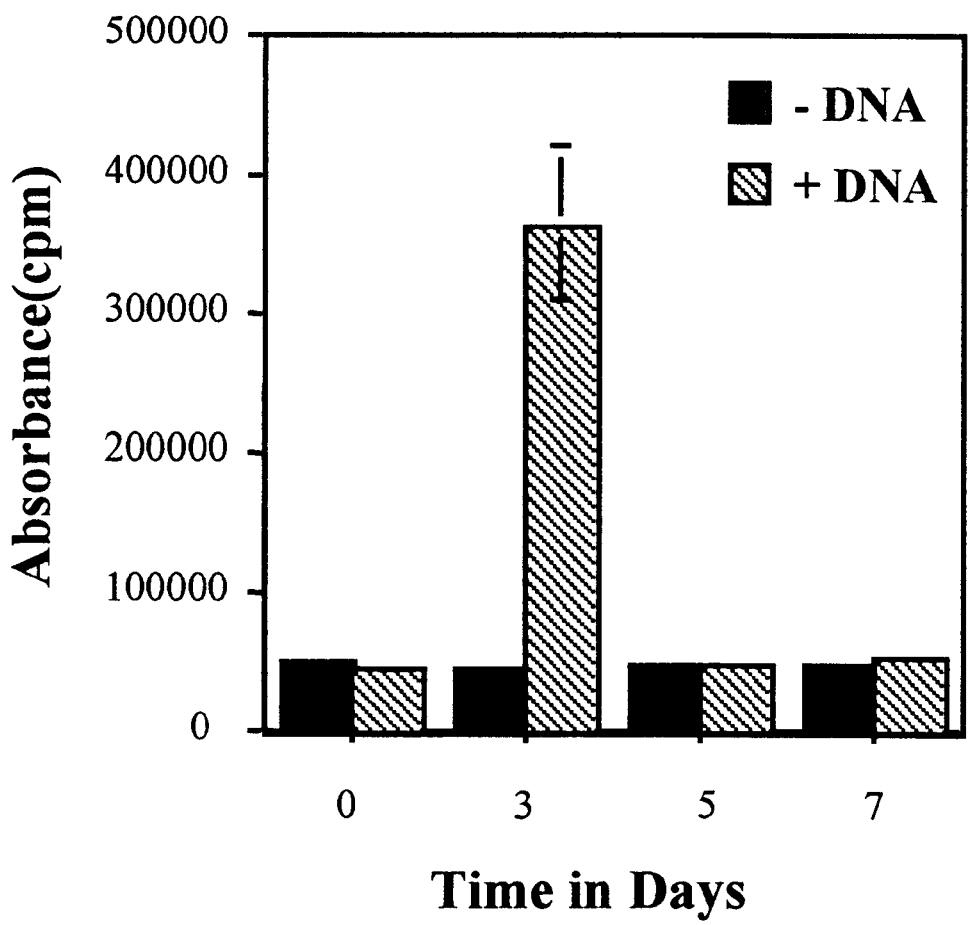
FIG. 3 depicts the time course of luciferase gene expression after direct in vivo electrotransfection with 100 $\mu$g of pGL3.

Significant luciferase activity was expressed at day 3 and 7 after the electrotransfection for kidneys and bladders, respectively (FIG. 3, 7). No luciferase activity was detected in animals transfected with PBS only as controls. Distant organs failed to show any luciferase activity. Effective gene transfer was obtained by the luciferase activity assay at day 3, indicating that the percutaneous electrotransfection into kidneys is feasible. The control kidneys that received PBS only did not show any activity. The most effective current in both kidneys and bladders proved to be at 100 volts direct current. Electrical current of 50 and 200 volts demonstrated weaker luciferase activities.

Figure 10:
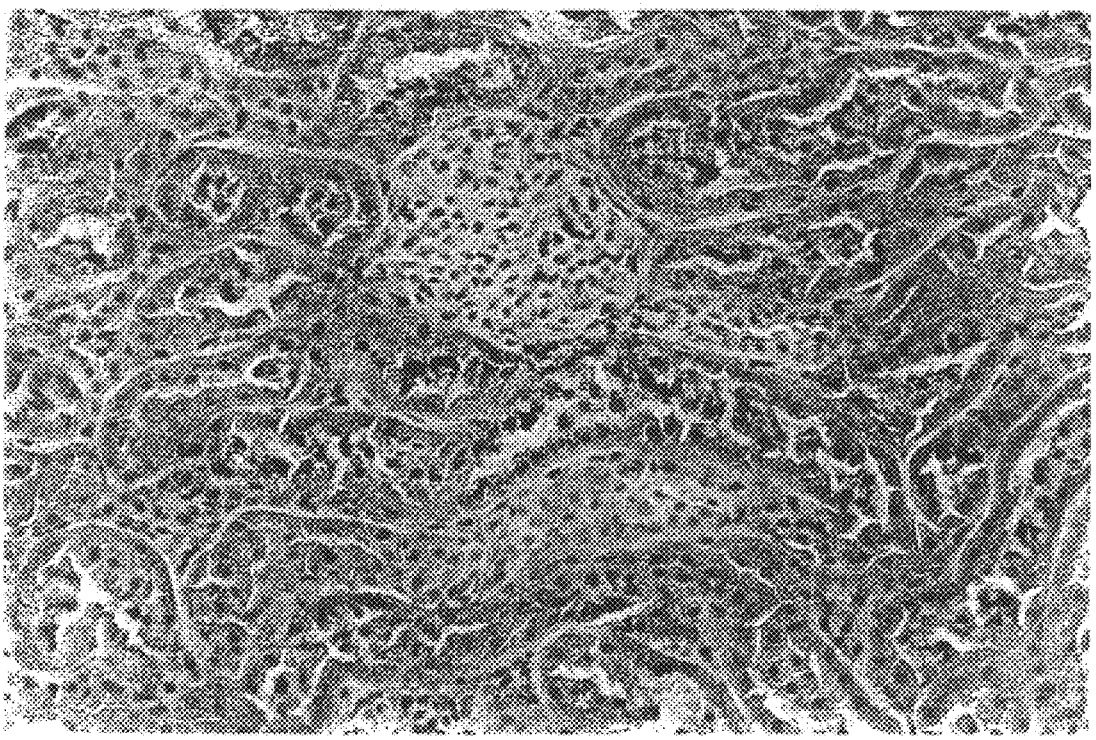
FIG. 10 depicts the immunocytochemical analysis of galactosidase expression using X-gal in kidney.
Figure 11:
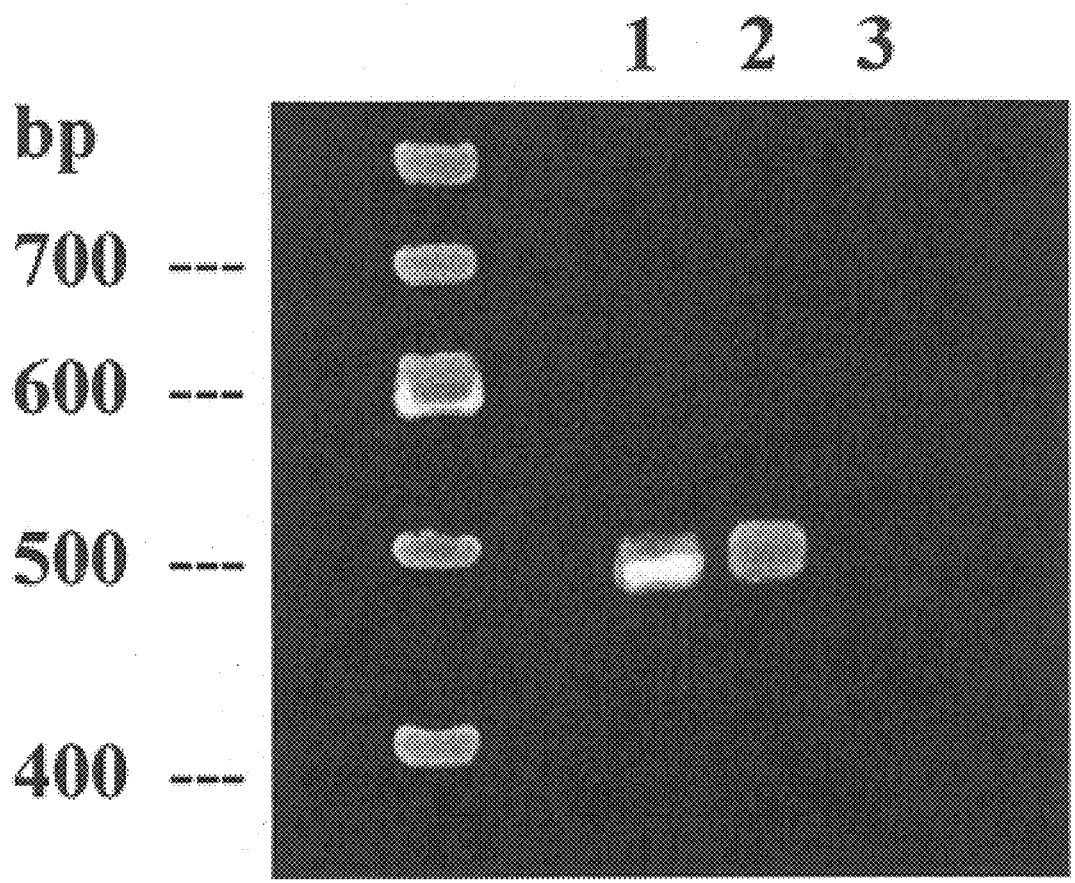
FIG. 11 depicts reverse transcription PCR products indicating the presence of $\beta$-galactosidase mRNA in transfected testis (lane 2). The control testis (lane 3) failed to show any $\beta$-galactosidase mRNA. The positive control, $\beta$-galactosidase-plasmid is depicted in lane 1.
Figure 12:
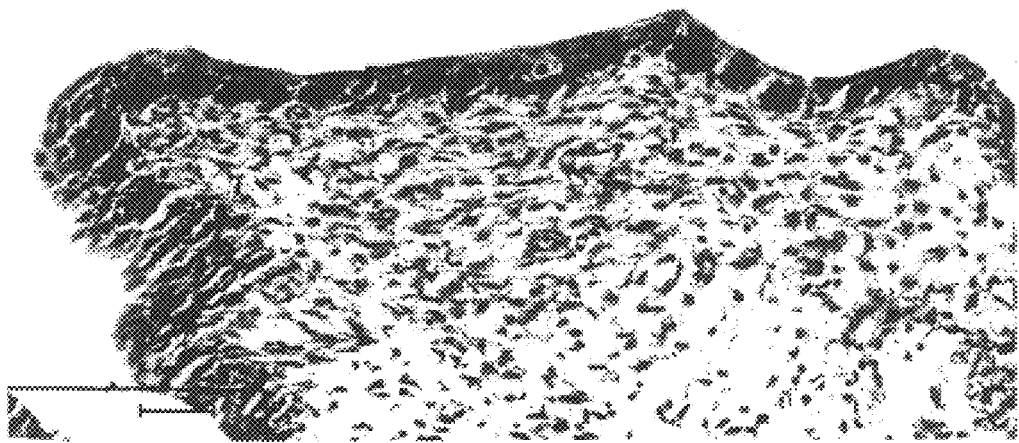
FIG. 12 depicts immunocytochemical analysis of $\beta$-galactosidase expression using $\beta$-galactosidase monoclonal antibody in bladders. Note the positive staining over the entire urothelial cell layer.
Figure 13:
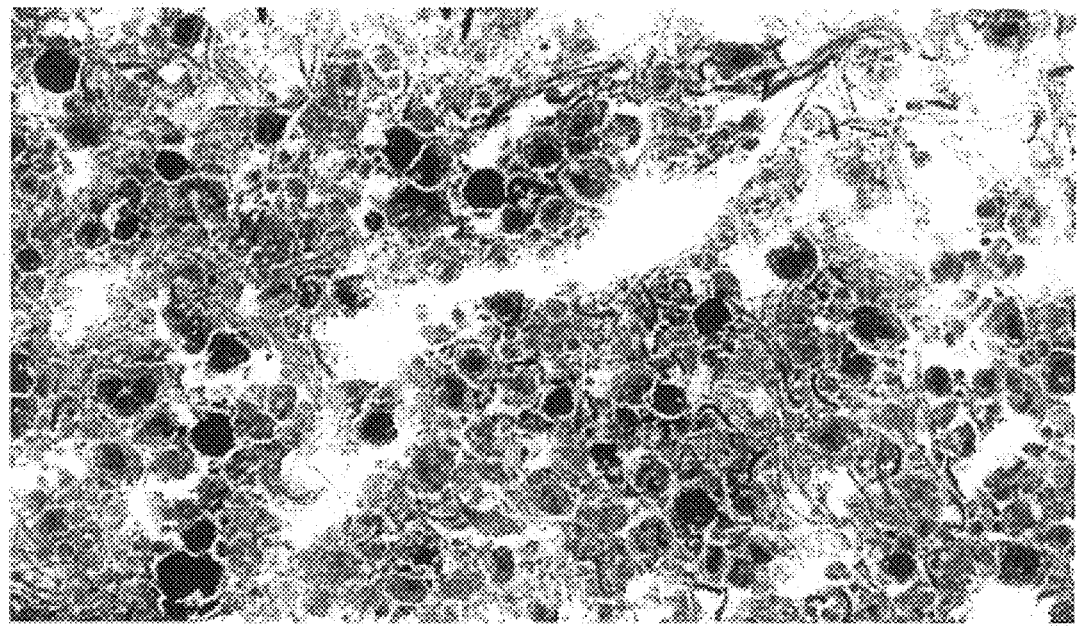
FIG. 13 depicts the histochemical analysis of $\beta$-galactosidase expression using X-gal in testis. Indigo blue staining was demonstrated in the interstitium and germ cells. Panel A is reduced from 100×. Panel B is reduced from 400×.
Figure 14:
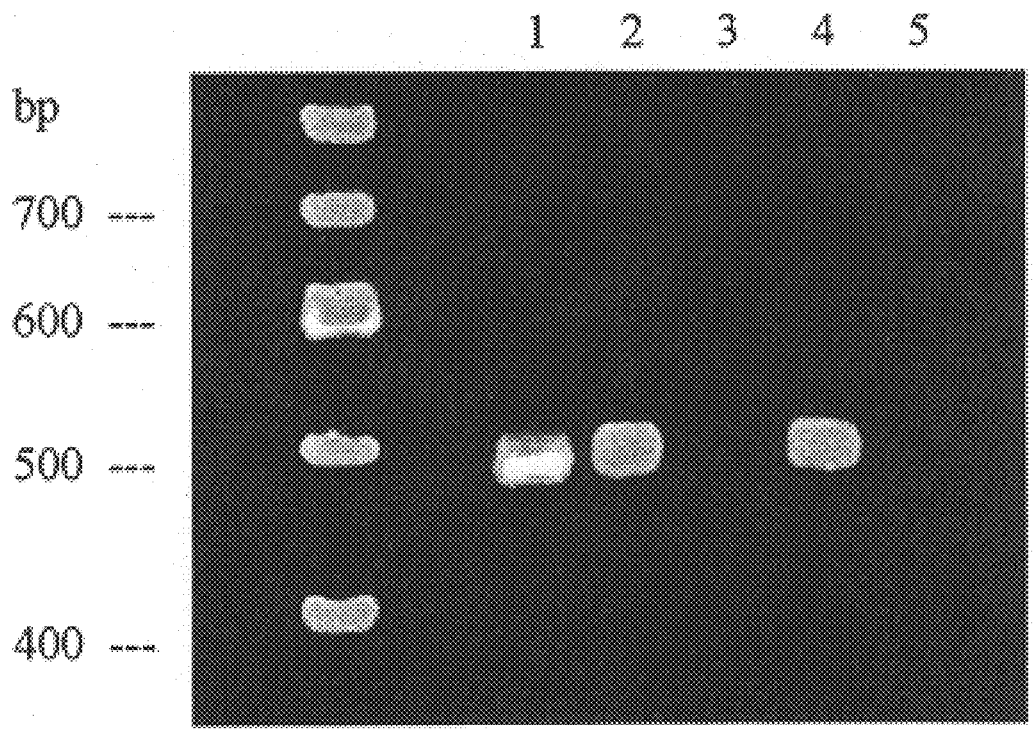
FIG. 14 depicts reverse transcription-PCR products corresponding to the predicted size of 500 base pairs that were obtained from RNA isolated from electrotransfected bladders (lane 2) and kidneys (lane 4). The control bladders (lane 3) and kidneys (lane 5) failed to show any $\beta$-galactosidase mRNA>The positive control, $\beta$-galactosidase plasmid was run in lane 1.

At retrieval, electrotransfected organs appeared normal grossly and histologically. β-galactosidase assays using both the x-gal and β-galactosidase antibody revealed similar results. A positive staining was confined to renal cortex while medulla stained negatively at day 3 post-transfection. In high power field (250×), renal tubular cells stained positively and other structures such as glomeruli, collecting ducts and interstitial cells stained negatively (FIG. 10). That is, β-galactosidase expression was noted only in renal tubular cells, while the glomuruli and stromal cells stained negatively. In bladder at day 7, the uroepithelial cell layer demonstrated positive stain. However, the submucosal and smooth muscle layers stained negatively. The PBS treated control kidneys, bladders and other distant organs failed to show any β-galactosidase activities (FIG. 3, 7).

RT-PCR products corresponding to the predicted size of 500 base pairs were obtained from RNA isolated from electrotransfected kidneys and bladders. In contrast, the PBS treated control kidneys and bladders failed to show any β-galactosidase mRNA by RT-PCR. These findings indicate that β-galactosidase mRNA was successfully transcribed in the electrotransfected kidneys and bladders. (FIG. 3, 5, 7)

The results of luciferase activity assays, immunocytochemical assays and RT-PCR indicate that effective gene transfer to both kidneys and bladders can be achieved by direct in vivo electrotransfection. However, the outcome of the luciferase activity reveals that gene transfer by electrotransfection is transient with maximal expressions at 3 and 7 days for kidneys and bladders, respectively. Davis et. al., in their study, compared two different vectors, pSV40-luc and pRSV-luc, in direct gene transfer into mouse skeletal muscle (Davis, H. L. et al., *Human Gene Therapy* 4: 151, 1993). Their results showed that pPSV-luc expression lasted and was still increasing at 60 days in mouse skeletal muscles, whereas the pSV40-luc resulted in an early peak at 3 days post-transfer and declined. They believe that the choice of viral promoters may play a role in the time course of expression.

Direct injection of plasmid DNA into organs including skeletal muscle, heart and liver has been performed with various results (Wolff, J. A. et al., *Science* 247: 1465, 1990, Davis, H. L. et al., *Human Gene Therapy* 4: 151, 1993; Wolff, J. A. et al., *Human Molecular Genetics* 1: 363, 1992; Hickman, M. A. et al., *Human Gene Therapy* 5: 1477, 1994). Injection of plasmid pRSVL in mouse skeletal muscle resulted in 19 months of persistence of plasmid DNA and luciferase expression (Wolff, J. A. et al., *Human Molecular Genetics* 1: 363, 1992). In the contrary, Hickman et al. delivered pCMVL expressing luciferase reporter gene directly into liver (Hickman, M. A. et al., *Human Gene Therapy* 5: 1477, 1994). Direct injection of pCMVL resulted in maximal luciferase expression at 24–48 hours.

The present results suggest that the gene expression of direct injection of plasmid DNA may vary between target tissue and cells. Our results agree with this. The time course of the peak luciferase expression differed between the kidneys and bladders. In this Example, a maximal gene expression occurred at 3 days post-transfection.

Other embodiments and uses of the invention will be apparent to those skilled in the art from consideration of the specification and practice of the invention disclosed herein. All U.S. Patents and other references noted herein for whatever reason are specifically incorporated by reference, as is U.S. Provisional Application No. 60/104,403. The specification and examples should be considered exemplary only with the true scope and spirit of the invention indicated by the following claims.

We claim:

1. A method for direct in vivo electrotransfection of a plurality of cells of a target tissue with a nucleic acid construct comprising the steps of:
   a) perfusing the target tissue with a transfection solution comprising a nucleic acid construct;
   b) surrounding at least a portion of said target tissue with an exterior electrode;
   c) placing one or more interior electrode with said target tissue; and
   d) applying an electric waveform through the exterior electrode and the interior electrode, thereby electrotransfecting said target tissue,
   wherein the exterior electrode is a non-planar sheet completely or partially surrounding the target tissue thereby causing the current flow to travel omnidirectionally to or from the interior electrode.

2. The method of claim 1 wherein the plurality of cells are selected from the groups consisting of hematopoietic cells, bone marrow cells, kidney cells, myocytes, hepatocytes.

3. The method of claim 1 wherein said target tissue is selected from the group consisting of organs, muscles, skin, blood vessel.

4. The method of claim 1 wherein said target tissue is an organ selected from the group consisting of heart, lung, kidney, liver, spleen, thymus, eye, pancreas, stomach, ovary, bowel, testicles, prostate, skeletal muscle, a prenatal fetus and combinations and portions thereof.

5. The method of claim 1 wherein said transfection solution is selected from the group consisting of physiological saline, phosphate buffered saline and mixtures thereof.

6. The method of claim 1 wherein said perfusing step is performed with a hollow perfusion needle.

7. The method of claim 1 wherein said exterior electrode is a pliant metal sheet.

8. The method of claim 1 wherein said exterior electrode is a wire mesh.

9. The method of claim 1 wherein said interior electrode is an insulated elongated electrode with an uninsulated tip.

10. The method of claim 9 wherein said insulated elongated electrode is an insulated wire or an insulated needle.

11. The method of claim 10 wherein said insulated needle is hollow.

12. The method of claim 1 wherein the electric waveform is an alternating current waveform or a direct current waveform.

13. The method of claim 12 wherein the electric waveform is a sine wave, a square wave, a sawtooth wave, a ramp wave, a reverse ramp wave and serial and parallel combinations thereof.

14. The method of claim 1 wherein the electric waveform comprises more than one electrical pulse.

15. The method of claim 1 wherein said electric waveform generator is a charged capacitor.

16. The method of claim 1 further comprising the step of applying a layer of biocompatible electrically conductive gel between said exterior electrode and said target tissue before the applying step.

17. The method of claim 1 wherein said electrotransfection comprise a plurality of electrotransfections applied over a period of between one hour and two weeks.

18. The method of claim 17 further comprising the step of perfusing said target tissue before each electrotransfection.

19. The method of claim 18 wherein one or more of said exterior electrode, interior electrode, and perfusion needle remains attached to the target tissue between electrotransfections.

20. The method of claim 18 wherein said interior electrode is repositioned between each electrotransfection.

21. A method for the treatment of a disorder in a patient by transfecting a target tissue in said patient with a DNA construct using the method of claim 1.

22. The method of claim 21 wherein the disorder is a genetic defect or a deficiency.

23. The method of claim 22 wherein the genetic defect is selected from the group consisting of LDL receptor defect and diabetes.

24. The method of claim 21 wherein the DNA construct comprise a gene selected from the group consisting of an LDL receptor, a hemoglobin gene and an insulin gene.

25. The method of claim 21 wherein the patient is selected from the group consisting of a fetus, a prenatal patient and a neonatal patient.

26. The method of claim 21 wherein the disorder is selected from the group consisting of a bacterial infection, a viral infection, graft verses host disease, host verses graft disease and an autoimmune disease.

27. The method of claim 26 wherein the DNA construct is selected from the group consisting of an antibacterial gene, an antiviral gene, or an immune response gene.

28. The method of claim 27 wherein said DNA construct is selected from the group consisting of an interferon gene, a histocompatibility gene, an immunoglobulin gene, and combinations thereof.

29. The method of claim 21 wherein said disorder is a neoplastic disorder.

30. The method of claim 29 wherein said DNA construct is selected from the group consisting of anti-oncogenes, anti-proliferative genes, and cytotoxic genes.

31. An apparatus for the in vivo electrotransfection of a target tissue comprising:

an exterior electrode;

an interior electrode;

a perfusion needle; and a transfecting solution;

wherein the exterior electrode is a non-planar sheet completely or partially surrounding the target tissue thereby causing a current flow to travel omnidirectionally to or from the interior electrode.

32. The apparatus of claim 31 wherein said exterior electrode is a pliant metal sheet and shaped to fit an outer surface contour of a target tissue.

33. The apparatus of claim 31 wherein the exterior electrode comprises a plurality of radial spokes of conducting material designed to encapsulate a target tissue.

34. The apparatus of claim 31 wherein said interior electrode is an insulated needle.

35. The apparatus of claim 31 wherein said insulating needle is also a perfusion needle.

36. The apparatus of claim 31 wherein said transfecting solution is phosphate buffered saline.

37. The apparatus of claim 31 wherein said apparatus is an endoscopic electrotransfection apparatus.

38. A kit for in vivo electrotransfection comprising:

a pliant electrode for encapsulating a target tissue;

an interior electrode;

a perfusion needle; and an electrotransfection solution, wherein the pliant electrode is a non-planar sheet completely or partially surrounding the target tissue thereby causing a current flow to travel omnidirectionally to or from the interior electrode.

39. The kit of claim 38 wherein said pliant electrode is a metal foil.

40. A method for the selective transfection of the renal cortex cells comprising the steps of:

perfusing a kidney with a transfection solution comprising a nucleic acid construct;

surrounding at least a portion of said kidney with an exterior electrode;

a age placing an interior electrode within said target tissue; and electrotransfecting said renal cortex cells through the exterior electrode and the interior electrode using an electric waveform generator, wherein the exterior electrode is a non-planar sheet completely or partially surrounding the kidney thereby causing a current flow to travel omnidirectionally to or from the interior electrode.

41. The method of claim 40 wherein said renal cortex cells are renal tubular cells.

42. The method of claim 40 wherein said method selectively transfects renal tubular cells without transfecting glomeruli cells, collecting duct cells, and interstitial cells.

43. The method of claim 40 wherein said electric waveform generator is a capacitor of about 1120 microfarads charged to about 100 volts.

44. A method for the selective transfection of uroepithelial cell layer of a bladder comprising the steps of:

perfusing said bladder with a transfection solution comprising a nucleic acid construct;

surrounding at least a portion of said bladder with an exterior electrode;

placing an interior electrode within said bladder; and electrotransfecting said uroepithelial cells through the exterior electrode and the interior electrode using an electric waveform generator, wherein the exterior electrode is a non-planar sheet completely or partially surrounding the bladder thereby causing a current flow to travel omnidirectionally to or from the interior electrode.

45. The method of claim 44 wherein said method selectively transfects said uroepithelial cell layer of a bladder without transfecting the submucosal and smooth muscle layers.

46. The method of claim 44 wherein said electric waveform generator is a capacitor of about 1120 microfarads charged to about 100 volts.

47. A method for direct in vivo electrotransfection of a subsegment of cells of a target tissue with a nucleic acid construct comprising the steps of:

a) perfusing the subsegment of the target tissue with a transfection solution comprising a nucleic acid construct;

b) surrounding at least a portion of said target tissue with an exterior electrode;

c) placing one or more interior electrode within said target tissue; and d) applying an electric waveform through the exterior electrode and the interior electrode, thereby electrotransfecting said target tissue, wherein the exterior electrode is a non-planar sheet completely or partially surrounding the target tissue thereby causing a current flow to travel omnidirectionally to or from the interior electrode.

* * * * *